(12) United States Patent
Wagner et al.

(10) Patent No.: US 10,632,149 B2
(45) Date of Patent: Apr. 28, 2020

(54) DRUG BASED ON MAGHEMITE FOR SIMULTANEOUS REDUCTION OF GASTROINTESTINAL SODIUM RESORPTION AND PHOSPHATE RESORPTION

(71) Applicants: CHARITÉ-UNIVERSITAETSMEDIZIN BERLIN, Berlin (DE); Susanne Wagner, Blankenfelde-Mahlow (DE)

(72) Inventors: Susanne Wagner, Blankenfelde-Mahlow (DE); Matthias Taupitz, Mahlow (DE); Joerg Schnorr, Dranienburg (DE); Monika Ebert, Blankenfelde-Mahlow (DE); Nicola Stolzenburg, Berlin (DE); Janna Glaeser, Bremen (DE); Harald Kratz, Berlin (DE); Ralf Hauptmann, Berlin (DE); Janni Breinl, Chemnitz (DE); Angela Ariza De Schellenberger, Berlin (DE); Ines Gemeinhardt, Berlin (DE)

(73) Assignee: CHARITE-UNIVERSITAETSMEDIZIN BERLIN, Berlin (DE)

( * ) Notice: Subject to any disclaimer, the term of this patent is extended or adjusted under 35 U.S.C. 154(b) by 0 days.

(21) Appl. No.: 15/540,067

(22) PCT Filed: Dec. 28, 2015

(86) PCT No.: PCT/DE2015/000608
§ 371 (c)(1),
(2) Date: Jun. 27, 2017

(87) PCT Pub. No.: WO2016/107619
PCT Pub. Date: Jul. 7, 2016

(65) Prior Publication Data
US 2017/0348351 A1 Dec. 7, 2017

(30) Foreign Application Priority Data

Dec. 29, 2014 (DE) .................. 10 2014 019 388

(51) Int. Cl.
*A61K 33/26* (2006.01)
*A61K 9/14* (2006.01)
*A61K 9/00* (2006.01)

(52) U.S. Cl.
CPC ............ *A61K 33/26* (2013.01); *A61K 9/0053* (2013.01); *A61K 9/143* (2013.01)

(58) Field of Classification Search
None
See application file for complete search history.

(56) References Cited

U.S. PATENT DOCUMENTS

| 6,174,442 B1 | 1/2001 | Geisser et al. |
| 2012/0263670 A1 | 10/2012 | Charmot et al. |
| 2014/0023611 A1 | 1/2014 | Lewis et al. |

FOREIGN PATENT DOCUMENTS

| CN | 103906523 A | 7/2014 |
| DE | 102011112898 | 3/2013 |

(Continued)

OTHER PUBLICATIONS

Labonte et al.: "Gastrointestinal Inhibition of Sodium-Hydrogen Exchanger 3 Reduces Phosphorus Absorption and Protects against Vascular Calcification in CKD", Journal of the American Society of Nephrology 26, Nov. 17, 2014.

(Continued)

*Primary Examiner* — Dominic Lazaro
(74) *Attorney, Agent, or Firm* — Fox Rothschild LLP

(57) ABSTRACT

The invention includes a substance based on nanocrystalline maghemite having a crystal size of between 0.5 and 4 nm, which is defined by a proportion of divalent iron ions less than five percent by weight of the total iron, and the transport (Continued)

Highly-resolved transmission electron microscopy
Octahedral maghemite crystal

Selected Area Electron Diffraction = SAED

| d(hkl) | Measured Values |
|---|---|
| 0.151nm | → (440) |
| 0.164nm | → (511) |
| 0.214nm | → (400) |
| 0.253nm | → (311) |
| 0.297nm | → (220) | of sodium and simultaneously phosphate in the gastrointestinal wall from the gastrointestinal contents into the bloodstream is reduced and thus can improve the imbalance of electrolyte and water and mineral balances of patients having impaired renal function when used orally in combination with suitable pharmaceutical adjuvants.

2 Claims, 4 Drawing Sheets

(56) References Cited

FOREIGN PATENT DOCUMENTS

| WO | 2013034267 | 3/2013 | |
|---|---|---|---|
| WO | WO-2013034267 A1 * | 3/2013 | ............ A61K 33/26 |

OTHER PUBLICATIONS

Nguyen et al: "Novel oral phosphate binder with nanocrystalline maghemite-phosphate binding capacity and pH effect", International Journal of Pharmaceutics, vol. 482, No. 1-2, Nov. 6, 2014.

Vethe et al: "Experimental Pathology", Nephrology Dialysis Transplantation, vol. 29, No. suppl 3, May 1, 2014(May 1, 2014), pp. iii201-iii208.

International Search Report dated Apr. 20, 2016 in PCT/DE2015/000608.

* cited by examiner

FIG. 2

Highly-resolved transmission electron microscopy
Octahedral maghemite crystal

Selected Area Electron Diffraction = SAED

| d(hkl) | Measured Values |
|---|---|
| 0.151nm → | (440) |
| 0.164nm → | (511) |
| 0.214nm → | (400) |
| 0.254nm → | (311) |
| 0.297nm → | (220) |

DRUG BASED ON MAGHEMITE FOR SIMULTANEOUS REDUCTION OF GASTROINTESTINAL SODIUM RESORPTION AND PHOSPHATE RESORPTION

CROSS REFERENCE TO RELATED APPLICATIONS

This U.S. Application is a National Stage Entry of PCT/DE2015/000608 filed on Dec. 28, 2015, which claims priority to German Application No.: 10 2014 019 388.8 filed Dec. 29, 2014, entitled "DRUG BASED ON MAGHEMITE FOR SIMULTANEOUS REDUCTION OF GASTROINTESTINAL SODIUM RESORPTION AND PHOSPHATE RESORPTION" the entirety of which is incorporated herein by reference.

The present invention relates to a medicinal product consisting of nanocrystalline maghemite with monocrystalline iron oxide nanoparticles having crystal diameters between 0.5 and 4 nm with adjuvants from the group of carbohydrates and alditols, characterized in that this medicinal product is administered orally for a simultaneous reduction of sodium intake and phosphate intake in the intestine and thus for reduced excretion via the kidneys and will thus improve the water, mineral and electrolyte balance in patients with renal insufficiency.

BACKGROUND OF THE INVENTION

Patients with impaired renal function are likely to have an unfavorable sodium balance and have hyperphosphatemia, since the kidney can no longer excrete the sodium and the phosphate in sufficient amounts. In addition, imbalances occur in the hormonal control of mineral and electrolyte balance. Sodium intake in the intestine leads secondarily to water retention in the body tissue, to a higher blood volume and to hypertension, which aggravates the renal disease. Excessively high serum phosphate levels lead to atherosclerotic vessel wall changes with increased risk of cardiovascular events such as stroke or myocardial infarction. New developments are aimed at inhibitors of sodium intake in the intestine or phosphate intake in the intestine. A substance that inhibits the NHE ($Na^{++}/H^+$ exchange) transport mechanism as set forth in patent publication number US 2012/0263670 leads to a significant reduction in sodium resorption in healthy rats, which is documented by the reduction of sodium excretion in the urine. According to the literature of Labonte et al., this group of substances, as set forth in patent publication number US 2012/0263670, leads to a reduction in sodium excretion through reduced sodium intake by 0.3 mmol compared to a control group and also to a reduction of phosphate excretion in initial pre-clinical in vivo studies in rats in an active compound co-feed mixed test in healthy animals (compare FIG. 4A and 4B in Labonte et al., 2014, Journal of the American Society of Nephrology 26, online publication doi: 10.1681/ASN.2014030317). This medicinal product according to Labonte et al., in a study of healthy rats, 2014, also leads to a minimal reduction in the phosphate resorption in the intestine and thus a reduction in urine excretion, in a study in healthy rats. However, the effect of this substance according to Labonte et al. 2014 does not cause a significant reduction in serum phosphate levels. According to Labonte, an increase in the dose or the use of a substance with a stronger effect leads to severe diarrhea. This shows a narrow therapeutic range of the substances according to Labonte et al., set forth in patent publication number US 2012/0263670. A substance which can simultaneously significantly reduce the serum phosphate level by inhibiting gastrointestinal resorption and which can inhibit sodium resorption and is not associated with increased stool volume and diarrhea is not known with this pronounced effect such as for the substance according to the invention here according to Example 1 and Example 2.

DESCRIPTION OF THE INVENTION

Surprisingly, a substance consisting of maghemite with a preparation according to Example 1 and adjuvants of mannitol, inulin and gum arabic, when administered orally, leads to a reduction in the gastrointestinal resorption of sodium and to a reduced excretion via urine in healthy rats as shown in Example 2. At the same time, the substance according to Example 1 leads to a reduction in the serum phosphate level in the dose tested according to Example 2, with no side effects such as diarrhea. This reduction in sodium resorption is surprisingly associated with a reduction in gastrointestinal phosphate resorption and leads to hypophosphatemia according to Example 2, which can not be explained by a pure chemical adsorptive effect of the phosphate on the iron oxide. The extent of the hypophosphatemia achieved according to Example 2 with the substance according to Example 1 exceeds by far the extent as would be explained by pure chemical adsorptive action of the iron oxide in the form of maghemite in the substance according to the invention, compared to the phosphate in the diet. The feed content of phosphorus is 0.7% (weight), thus is theoretically available in an amount of 2.1% phosphate (weight). The addition of the substance according to Example 1, based on the weight of iron as a component of the maghemite of 0.25%, even in the case of optimum phosphate binding, does not lead to sufficient free phosphate being available for the organism's gastrointestinal intake. Compared to the literature according to Labonte et al., the effect of the substance according to the invention based on maghemite on sodium resorption through Example 1 is three times higher (reduction of the sodium excretion by 1 mmol) than a specifically developed inhibitor according to patent publication number US 2012/0263670. For the substance according to the invention according to Example 1, this reduction of sodium resorption and renal excretion takes place without side effects such as diarrhea as described for the substance according to publication number US 2012/0263670 and Labonte et al. 2014. Thus, for the substance according to Example 1, a very high therapeutic margin is obtained in contrast to the substance according to publication number US 2012/0263670 and Labonte et al. 2014. The in vivo studies according to Example 2 show that the urine volume is not significantly reduced and the weight of the stool is not significantly increased. This shows that the effect found here is not associated with side effects. The substance shown here according to the invention differs from the claims of the invention DE 102011112898 with regard to the construction of the primary and secondary sheaths. The substance according to the invention in DE 102011112898 is defined by primary magnetite crystal formation alone in the presence of alditols or monomeric and dimeric carbohydrates. The substance newly illustrated according to the invention in Example 1 is defined by simultaneous preparation and crystal formation in the presence of an alditol and a fructan. The substance is therefore primarily determined by the fructan, here inulin. In patent DE 102011112898, this variant in Example 5 was described as rather ineffective in the phosphate binding, and therefore it is not obvious that a substance produced as in Example 1 has effects which cannot be foreseen in an in-vivo test. However, the substance according to Example 1 differs from the substances and examples of patent DE 102011112898 to the effect that a polymer as in Example 1 is present directly in the primary crystal formation. According to the invention, this was not set forth in patent DE 102011112898. In a simulated gastrointestinal passage, the substance according to Example 1 is distinguished from Comparison Example 1 by the fact that with an excess of inorganic phosphate in the incubation solution, the phosphate binding capacity is 60% higher for the substance according to Example 1 than for the substance according to the Comparison Example 1. This technical feature of the substance according to Example 1 demonstrates that the primary incubation of the alditols and carbohydrates at a pH above 11 before mixing with the iron salts leads to a chemical alteration of these alditols and carbohydrates which leads to a substance which differs from the substance according to Comparison Example 1. Moreover, surprisingly, the substance according to Example 1 is characterized by a higher stability, which is evident by the fact that the proportion of free iron is lower in the gastrointestinal passage than for the substance according to Comparison Example 1. This influence on the renal sodium excretion by the substance according to the invention according to Example 1 is not accompanied by a reduction in the serum sodium level. The total weight of the feces does not differ from the comparison groups. Likewise, the substance according to the invention according to Example 1 has no influence on potassium excretion and protein excretion and on the urine volume in the 24 hours collective experiment. The Velphoro® with the active substance sucroferric oxyhydroxide is comparable to the substance according to the invention shown here according to Example 1 a special form of the iron oxide with adjuvants from the group of carbohydrates. The active substance of Velphoro® is, according to the patent published under the number WO 97/22266, the iron oxyhydroxide akaganeit and the substances used in the production are sucrose and starch. The Velphoro® causes a significant reduction in gastrointestinal sodium resorption. However, no effect on the serum phosphate level is seen in the dose examined here. This demonstrates that such a strong effect on gastrointestinal phosphate resorption cannot be achieved with any type of iron oxide in combination with a carbohydrate. In fact, the effect of the substance according to the invention according to Example 1 is superior to Velphoro® in this combined reduction in phosphate resorption and the simultaneous reduction in sodium resorption. Thus, it can only be assumed that the substance according to Example 1 is surprisingly suitable for selectively reducing the intake of sodium and phosphate from the intestine, which is documented in a highly significant reduction in the excretion of sodium via the kidney and in a highly significant reduction in serum phosphate levels. The substance according to Example 1 is in fact superior not only to the medicinal products Velphoro®, Renvela® and Fosrenol®, but also to new special transport inhibitors as substances described in patent publication US 2012/0263670 and publication Labonte et al. 2014, and in patent WO 2012/0006475 A1. The effect of the substance according to the invention according to Example 1 on gastrointestinal phosphate intake is so strong that the healthy rats fall into a hypophosphatemia, which obviously resulted in the weight development to a significantly lower weight of the rats at the end of the experiment. This side-effect, which is caused solely by the very high desired effect, can be easily remedied by further dose reduction, which confirms the superiority of the substance according to the invention set forth herein to other substances according to the prior art. It was determined that the combination of the adjuvants used here alone had a significant influence on renal sodium excretion compared to the control group. The substance according to the invention is prepared in a wet chemical aqueous via the primary precipitation of magnetite in the presence of iron (II) chloride and iron (III) chloride at temperatures below 10° C. and in the presence of mannitol and inulin. After primary crystallization, the crystalline magnetite is actively oxidized to maghemite by means of hydrogen peroxide at temperatures above 50° C. and then the unreacted starting materials and undesirable reaction products are removed by means of dialysis, diafiltration or even ultrafiltration. Mixtures of other alditols, monomeric hexoses, monomeric pentoses and their polymers are conceivable. The production described here according to the invention leads to a chemical yield, based on the proportion by weight of iron and the proportion of iron in the final product of more than 60%, and >90 of the crystals are between 0.5-4 nm in size, as determined by TEM. According to the invention, the substance causes a reduction in sodium intake in the intestine, which is accompanied by a significant reduction in sodium excretion in the urine, without influencing the serum sodium level. Surprisingly, the substance in the dose tested here also leads to a reduction in the serum phosphate level, which cannot be explained by a pure adsorptive effect as described in patent DE 102011112898, since with a feed phosphate content of 2.1%, co-feeding of the substance according to example 1 means an addition of 0.25% iron and therefore the rat still has sufficient nutrient phosphate for a balanced phosphate metabolism. On the basis of the publication according to Labonte et al., it is assumed that an influence on the sodium resorption with a reduction of the sodium resorption in the intestine also leads to a hitherto unknown influence on phosphate resorption. This mutual influencing of both transport processes is surprisingly found here for the substance according to Example 1. Thus, the substance according to Example 1 is also distinguished by the fact that a significant reduction of the gastrointestinal sodium resorption is demonstrated by reduced renal sodium excretion with unchanged serum sodium level simultaneously with a significant reduction in the serum phosphate level. This dramatic effect on the serum phosphate level is not even found for a selective inhibitor of the gastrointestinal phosphate transporters, as shown in patent publication WO 2012/0006475 A1 Example57 on page 758. Thus, the substance according to the invention shown here is characterized by an inhibition of electrolyte transport processes and mineral transport processes, in this case sodium and phosphate, in the intestinal wall, which is superior to the substances currently under development and authorized, and this is should be suitable for regulating the sodium, water and phosphate balance in patients having impaired renal function in per oral administration in pharmaceutically known dosage forms. Compared to substances which have been authorized and are under development, it can be expected that the substance according to the invention of the present invention has a better effect with less side effects in the application for regulating the phosphate and sodium content in patients having impaired renal function. In addition to the adjuvants from the group of alditols and carbohydrates shown here, the production and application of the maghemite-based nanocrystals for the reduction of gastrointestinal sodium and phosphate resorption can be carried out using conventional known pharmaceutical adjuvants and also active ingredients. In addition to the substance according to the invention according to Example 1, the crystals may also contain, in addition to iron, other metals, metal hydroxides and metal oxyhydroxides. An application of the substance according to the present invention here is intended to reduce gastrointestinal sodium resorption and, at the same time, phosphate resorption with oral administration, and thus lead to an improvement in the water and electrolyte balance in patients having impaired renal function, which secondarily leads to a lowering of blood pressure and vessel wall calcification and thus improve the risk of cardiovascular diseases such as stroke and myocardial infarction in patients with renal impairment. The properties of the substance and the effectiveness of the in vivo application are illustrated by means of drawings.

DESCRIPTION OF THE DRAWINGS

FIG. 1A and FIG. 1B:

The result of the in vivo tests according to Example 2 in healthy rats is shown. Active ingredients were admixed to the feed and urine was collected in a metabolic cage for 24 hours and blood was collected from the animals. FIG. 1B shows the serum phosphate level. Compared to known active ingredients for regulating the mineral content in patients having impaired renal function, only the active substance according to Example 1 simultaneously leads to a significant influence on the sodium balance and the serum phosphate level.

FIG. 2:

A highly-resolved transmission electron microscope image of a typical octahedral maghemite crystal according to the invention of the substance produced according to Example 1 is shown, wherein the longest extension of the maghemite crystal is only 3.5 nm. The selective electron diffraction (SAED) leads to a diffraction pattern which is typical for magnetite-maghemite crystals.

FIG. 3A and FIG. 3B:

In comparison, the size distribution of the crystals is shown based on a size evaluation of the longest diameter of the crystals based on transmission electron microscope images.

FIG. 4A and FIG. 4B:

EXAMPLES

Figure 1A:
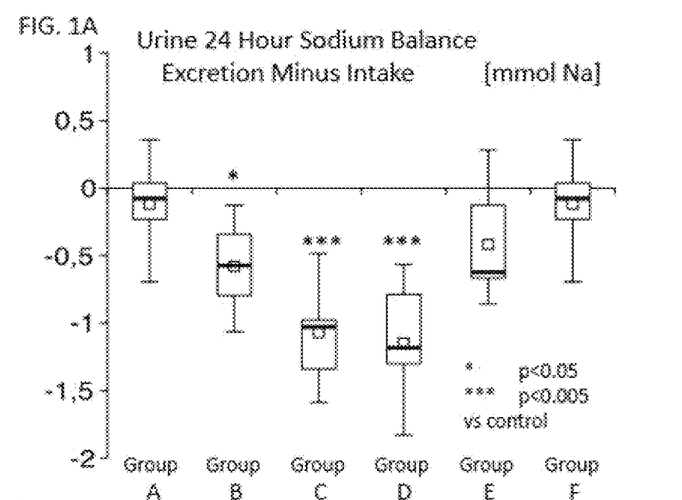
FIG. 1A shows the sodium balance calculated from sodium urine excretion minus the feed sodium intake.
Figure 1B:
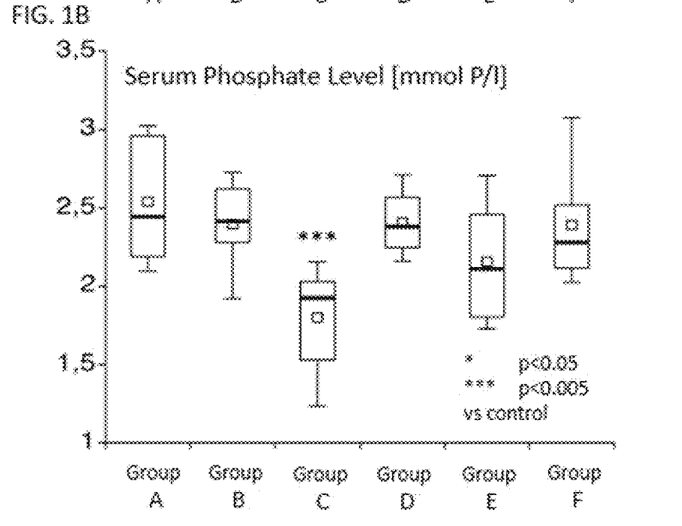
Figure 2:
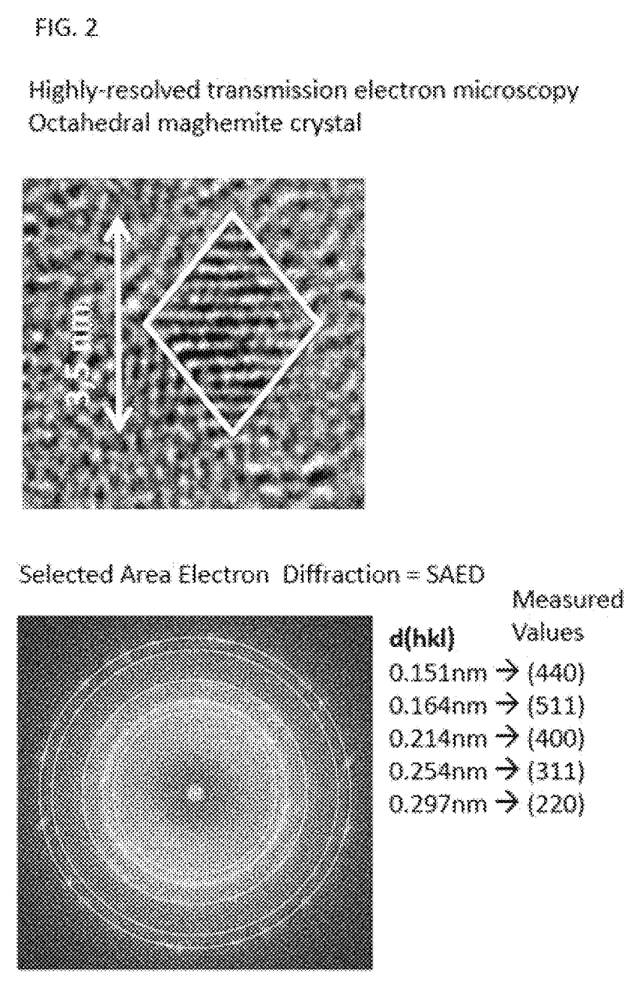
Figure 3A:
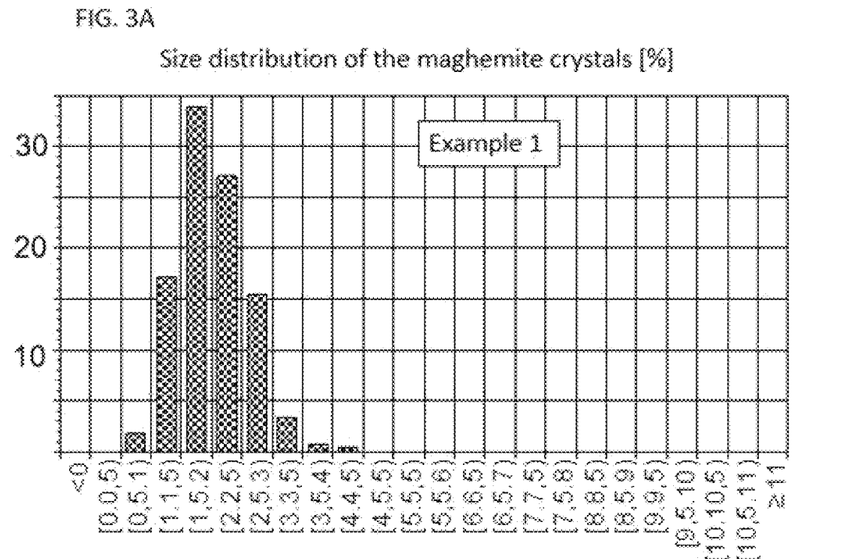
FIG. 3A shows the size distribution for the substance according to Example 1 and this shows a very uniform size distribution without a proportion of very large crystals. In comparison.
Figure 3B:
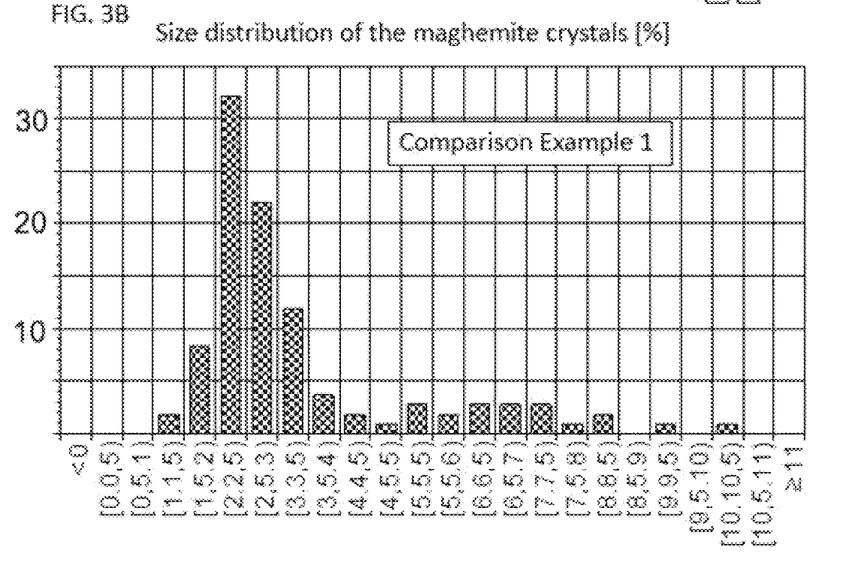
FIG. 3B shows the size distribution of the substance according to Comparison Example 2 and here it can be seen that a considerable proportion of crystals is present over a size of 4 nm—
Figure 4A:
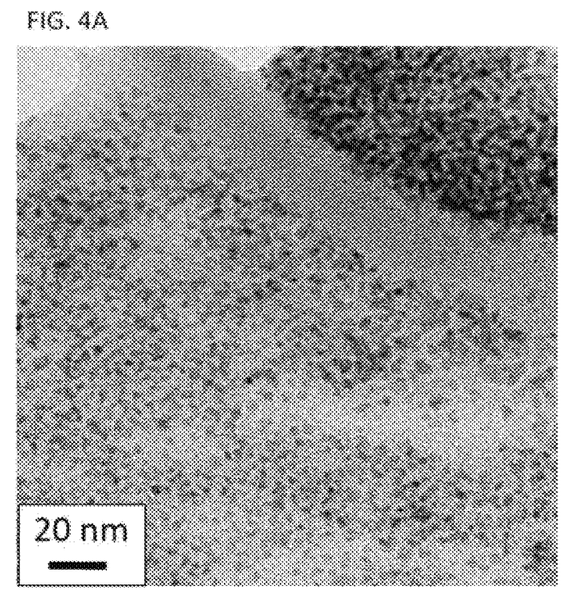
FIG. 4A shows a representative section of a transmission electron microscope image of the substance according to Example 1, which demonstrates that the substance according to Example 1 is a dispersion of very uniform maghemite crystals without large crystals or aggregates.
Figure 4B:
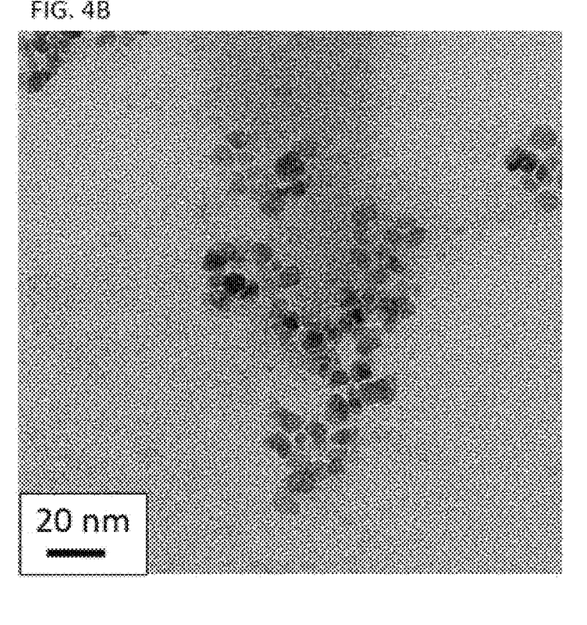
FIG. 4B shows a representative section of a transmission electron microscope image of the substance according to Comparison Example 1. Here, very large individual crystals are found in a not inconsiderable proportion. Overall, the crystallinity is shown to be inferior to that of the substance according to Example 1.

Method for the determination of phosphate binding capacity in a simulated gastrointestinal passage with excess of inorganic phosphate A 100 mM solution of sodium dihydrogen phosphate (Sigma-Aldrich No. 04269) was prepared in 0.1 M hydrochloric acid. The solution was heated to 37° C. and maintained at this temperature. 40 ml of this solution was transferred with the iron-containing phosphate binder in a quantity to obtain a 40 mM solution based on iron and thus a molar ratio in the incubation solution of inorganic phosphate to iron of 1:0.4. The pH was adjusted to 1.2 by means of hydrochloric acid using a titrator. An aliquot of 0.5 ml was withdrawn after each incubation for one hour and then the pH value was determined in the steps pH 2.5, 4.5, 7.0, 7.5 by means of the ammonium molybdate method photometrically by means of titrator with the extinction of 880 nm in the filtrate after centrifugation through a 3 kD CentriPrep® filter (regenerated cellulose). The free complexable iron content of the filtrate was determined photometrically by means of the orthophenanthroline method with the extinction of 520 nm.

Comparison Example 1

A maghemite-based phosphate adsorbent was prepared according to Example 1 patent international publication number WO 2013/034267 A1. 7.55 g of iron (III) chloride hexahydrate (Sigma-Aldrich, No. 31232) was dissolved in 50 ml of bi-distilled water cooled to 4° C. (solution A). To solution A, 3.2 g of iron (II) chloride tetrahydrate (Sigma-Aldrich No. 44939) was added and dissolved (solution B). In addition, 25 g of D-mannose (Sigma-Aldrich, No. 63582) was dissolved in bi-distilled water cooled to 4° C. (solution C). Solution B and C were combined and stirred for 2 min (solution D). 100 ml of 1.5 M NaOH (cooled to 4° C.) was added to solution D, and the resulting mixture was stirred for 5 min at 4° C. until a homogeneous colloid was formed (about 5 min) and then heated to 60° C. and stirred again at 60° C. for 15 min. During 15 minutes, the solution was cooled to room temperature while stirring and reduced to 100 ml by ultrafiltration (10 kD, Spectrum, Hollow Fiber, PES). The solution was dialyzed by means of dialysis tubes (12-14 kD cutoff regenerated cellulose, Spectra Por) 5 times against 2 liters of bi-distilled water until no iron and chloride was detectable in the filtrate. The colloidal solution present after the dialysis in a total quantity of 200 ml was mixed with 0.1 g of mannose, 3 g of gum arabicum (Acaciabaum Reagent Grade, Sigma G9752) and 3 g of inulin (Sigmaaldrich 12255, Chicory), which together had been dissolved in 25 ml of bi-distilled water. This dispersion was stirred for 3 min and filled up to 1 l with 100% ethanol. The nanoparticles were thus precipitated and additionally centrifuged at 800 rcf. The sediment was dried overnight at 60° C. The resulting dry substance was finely pulverized to a powder. The thus resulting powder has an iron content of 157 mg/g of dry substance at 2.04% content of bivalent iron relative to the total iron. The evaluation of 500 crystals leads to an average longest diameter of 3.4+1.9 nm with a proportion of 90% of the crystals smaller than 10 nm, however with a proportion of <20% of the crystals between 5 and 10 nm.

TABLE 3

Phosphate binding capacity at incubation 100 mM PO4 to 40 mM Fe for Comparison Example 1.

| PH | Phosphate binding capacity [mg PO4%/mgFe | free iron weight proportion % of initial weight |
|---|---|---|
| 1.2 | 670 | 26 |
| 2.5 | 790 | 6 |
| 4.5 | 910 | <1 |
| 7 | 950 | <1 |
| 7.5 | 970 | <1 |

TABLE 2

Size distribution of the
iron oxide crystals based on the
evaluation of 500 crystals in the
transmission electron microscope
image of the sample according to
Comparison Example 1.

| Size longest diameter [nm] | Size distribution proportion in % of the total count |
| --- | --- |
| 0.0-<0.5 | 0 |
| 0.5-<1.0 | 0 |
| 1.1-<1.5 | 2 |
| 1.5-<2.0 | 8 |
| 2.0-<2.5 | 32 |
| 2.5-<3.0 | 22 |
| 3.0-<3.5 | 12 |
| 3.5-<4.0 | 4 |
| 4.0-<4.5 | 2 |
| 4.5-<5.0 | 1 |
| 5.5-<6.0 | 3 |
| 6.0-<6.5 | 2 |
| 6.5-<7.0 | 3 |
| 7.0-<7.5 | 3 |
| 7.5-<8.0 | 3 |
| 8.0-<8.5 | 1 |
| 8.5-<9.0 | 0 |
| 9.0-<9.5 | 1 |
| 9.5-<10.0 | 0 |
| 10.0-<10.5 | 1 |

TABLE 3

Phosphate binding capacity at
incubation 100 mM PO4 to 40 mM Fe for Example 1.

| PH | Phosphate binding capacity [mg PO4%/mgFe] | free iron weight proportion % of initial weight |
| --- | --- | --- |
| 1.2 | 1185 | 8 |
| 2.5 | 1502 | <1 |
| 4.5 | 1734 | <1 |
| 7 | 1577 | <1 |
| 7.5 | 1605 | <1 |

TABLE 4

Size distribution of
the iron oxide crystals based
on the evaluation of 500
crystals in the transmission
electron microscope image of
the sample according to
comparative Example 1.

| Size Longest diameter [nm] | Size distribution proportion in % of the total count |
| --- | --- |
| 0.0-<0.5 | 0 |
| 0.5-<1.0 | 2 |
| 1.1-<1.5 | 17 |
| 1.5-<2.0 | 34 |
| 0-<2.5 | 27 |
| 2.5-<3.0 | 15 |
| 3.0-<3.5 | 3 |
| 3.5-<4.0 | 1 |
| 4.0-<4.5 | 1 |

Example 1

50 ml of water are cooled in an ice-water bath to temperature equilibrium. This is followed by successively dissolving 3.2 g of iron (II) chloride tetrahydrate and 7.55 g of iron (III) chloride hexahydrate=Solution 1. In another vessel, 25 g of D-mannitol and 5 g of inulin are dissolved in 100 ml of equally cooled 1.5 M sodium hydroxide solution=Solution 2. Solution 1 is poured rapidly into solution 2 and stirred further in ice-water cooling for 15 min. 3 ml of 30% hydrogen peroxide solution are then added, stirred for 5 minutes and then heated to 60° C. with stirring and stirred for a further 15 minutes. The sample is spontaneously cooled to room temperature and purified by means of dialysis against water and the retentate is centrifuged for 10 minutes at 4500 rpm (rotor radius 15 cm). The supernatant is transferred with 3 g of gum arabic, and the resulting solution is concentrated in a rotary evaporator and then freeze-dried. The resulting reddish brown powder has an iron content of 190 mg/g and a proportion of divalent iron <1%. The crystal size detected by TEM is between 0.5 and 4 nm for over 90% of the crystals. The electron diffraction pattern reveals a diffraction pattern characteristic of maghemite according to HKL classification: 220 plane=0.297 nm; 311 plane=0.254 nm; 400 plane=0.214 nm; 511 plane=0.164 nm; 440 level=0.151 nm. The evaluation of 500 crystals gives an average longest diameter of 3.0±0.6 nm with a proportion of 90% of the crystals smaller than 4.5 nm.

Example 2

Male rats of the breed Sprague Dawley from Charles River were used at the beginning of the experiment with weight of 200 g (n=8) per group listed below. The animals received feed ad libitum Altromin 1324 (powder form) in the first week of experiment (week 1) without active ingredient (0.7% phosphorus and 0.2% sodium relative to weight). Then for another 4 weeks (week 2-5), the feed mentioned above ad libitum with active substance additive. On the last day of each experiment week, the animals were kept individually in a metabolic cage for 24 hours (day 6 to day 7). Feces and urine were collected. Blood was obtained only on the last collection day. Blood and urine samples were examined by Synlab GmbH.

The groups received as follows from week 2-5 additives per 100 g feed Group A control—no additives Group B adjuvants—addition of 0.2 g of mannitol and each 0.9 g of inulin and gum arabic Group C Example 1—based on iron as an additive to the feed 250 mg of iron Group D Velphoro®—based on iron as an additive to the feed 250 mg of iron Group E Fosrenol®—based on lanthanum as an additive to the feed 250 mg lanthanum Group F Renvela®—based on Sevelamer carbonate 500 mg The results for the 24 hours collection period on the last day of the experiment (5 weeks total experiment and 4 weeks of active ingredient feeding) are as follows:

TABLE 4

Results of study according to Example 2 Data collection Day 7 Week 5

| Group A | Group B | Group C | Group D | Group E | Group F |
|---|---|---|---|---|---|
| Body weight (g) | | | | | |
| 438 ± 29 | 391 ± 33* | 375 ± 31** | 404 ± 28 | 374 ± 42*** | 466 ± 25 |
| Feed intake 24 hours (g) | | | | | |
| 18.75 ± 4.0 | 23.5 ± 4.6 | 25.3 ± 2.6* | 26.6 ± 4.5 | 21.6 ± 4.7 | 18.4 ± 2.9 |
| Sodium intake 24 hours [mmol] | | | | | |
| 1.76 ± 0.38 | 2.20 ± 0.43* | 2.37 ± 0.24*** | 2.50 ± 0.42*** | 2.03 ± 0.44 | 1.72 ± 0.27 |
| Sodium excretion Urine 24 hours [mmol] | | | | | |
| 1.64 ± 0.19 | 1.53 ± 0.21 | 1.3 ± 0.36 | 1.43 ± 0.23 | 1.61 ± 0.26 | 1.73 ± 0.14 |
| Sodium balance Intake feed minus excretion Urine 24 hours [mmol] | | | | | |
| −0.12 + 0.38 | −0.58 + 0.34* | −1.07 + 0.40** | −1.15 + 0.46*** | 0.42 + 0.44 | 0.01 + 0.37 |
| Feces excretion 24 hours Weight [g] | | | | | |
| 14.1 ± 3.0 | 12.9 ± 1.6 | 14.6 ± 3.2 | 17.1 ± 6.2 | 13.1 ± 2.6 | 14.7 ± 3.1 |
| Urine volumes 24 hours [ml] | | | | | |
| 24.9 ± 5.5 | 16.7 ± 5.6 | 17.4 ± 6.9 | 16.1 ± 3.6 | 21.3 ± 9.4 | 26 ± 8.3 |
| Serum sodium [mmol] | | | | | |
| 141 ± 1.4 | 140 ± 1.5 | 140 ± 1.5 | 141 ± 1.5 | 140 ± 1.0 | 142 ± 2.2 |
| Serum phosphate [mmol] | | | | | |
| 2.54 ± 0.40 | 2.42 ± 0.30 | 1.80 ± 0.37 | 2.41 ± 0.21 | 2.16 ± 0.39 | 2.39 ± 0.4 |

A statistical comparison of the analysis values of the control group with the active substance groups was carried out using the Prism 5.0f® program with the test One-Way Anova and Dunnett's postprocessing (* $p<0.05$;  $p<0.01$; * $p<0.005$).

Example 3

Reduction of Renal Osteodystrophy on the Animal Model of the Uraemic Rat by Co-Feeding the Substance According to the Invention according to 1

An uremia in rats (Sprague-Dawley, male, n=6, Charles River) is generated by co-feeding adenine (0.3% additional weight fraction, feed Altromin C100, it 1.2% phosphorus and 1.2% calcium for a period of 10 weeks.

After this 10-week period, the adenine was discontinued and 3 animals were still given the above-mentioned diet for 4 weeks without active ingredient (control group) and the other 3 animals then received the above-mentioned diet supplemented with 0.125% by weight of the iron according to the invention according to Example 1 (active ingredient group).

After this second 4-week period, the animals were killed and the thigh bones removed and the length determined (by right and left sides a total of n=6 bones). There was a significant difference in the diaphyseal thickness of the corticalis by means of (micro-computer tomography determined) 0.42 +0.08 mm for the control group and 0.59 +0.12 mm for the active substance group.

CITATIONS INCLUDED IN THE DESCRIPTION

Citations Patent Literature

US 2012/0263670
DE 102011112898
WO 2012/0006475 A1
WO 97/22266

Citations Non-patent Literature

Labonte et al. 2014 Journal of the American Society of Nephrology 26, online publication doi: 10.1681/ASN.2014030317

The invention claimed is:

1. A method for the preparation of maghemite crystals having a crystal size in the range of 0.5 to 4 nm and a magnetite proportion of less than 5 parts by weight of a hundred defined by the weight proportion of divalent iron ions on the total iron content, wherein the method includes the steps of:
    S1: preparing a first aqueous solution of sodium hydroxide having a pH value of 10-15, wherein the first aqueous solution further includes one or more alditols and one or more carbohydrates and wherein the first aqueous solution has a temperature of 0 to 10° Celsius;
    S2: preparing of a second aqueous solution including chloride ions, iron-II salts and iron-III salts, wherein the second aqueous solution has a temperature of 0 to 10° Celsius;
    S3: preparing a mixture of the first aqueous solution and the second aqueous solution, wherein the mixture has a temperature of 0 to 10° Celsius;
    S4: adding a hydrogen peroxide solution to the mixture obtained in step S3, and then heating to above 50° C.; and wherein magnetite crystals formed in step S4 are oxidized to maghemite crystals.

2. The method of claim 1, wherein the first aqueous solution includes inulin, gum arabic and mannitol.

* * * * *

UNITED STATES PATENT AND TRADEMARK OFFICE
CERTIFICATE OF CORRECTION

PATENT NO. : 10,632,149 B2
APPLICATION NO. : 15/540067
DATED : April 28, 2020
INVENTOR(S) : Susanne Wagner et al.

Page 1 of 1

It is certified that error appears in the above-identified patent and that said Letters Patent is hereby corrected as shown below:

On the Title Page

After (71), delete "; Susanne Wagner, Blankenfelde-Mahlow (DE)"

Signed and Sealed this
Second Day of June, 2020

Andrei Iancu
*Director of the United States Patent and Trademark Office*